US009283023B2

(12) United States Patent
Baron et al.

(10) Patent No.: US 9,283,023 B2
(45) Date of Patent: Mar. 15, 2016

(54) HAND-HELD CAUTERY DEVICE

(75) Inventors: Fred E. Baron, Largo, FL (US);
Alexandr Reznik, St. Petersburg, FL (US)

(73) Assignee: BOVIE MEDICAL CORPORATION, Clearwater, FL (US)

( * ) Notice: Subject to any disclaimer, the term of this patent is extended or adjusted under 35 U.S.C. 154(b) by 910 days.

(21) Appl. No.: 13/158,806

(22) Filed: Jun. 13, 2011

(65) Prior Publication Data
US 2012/0316554 A1     Dec. 13, 2012

(51) Int. Cl.
A61B 18/04     (2006.01)
A61B 18/08     (2006.01)
A61B 17/00     (2006.01)
(Continued)

(52) U.S. Cl.
CPC .......... *A61B 18/08* (2013.01); *A61B 2017/0023* (2013.01); *A61B 2017/00734* (2013.01); *A61B 2018/1226* (2013.01); *A61B 2019/307* (2013.01); *A61B 2019/4873* (2013.01)

(58) Field of Classification Search
CPC ...... A61B 18/08; A61B 18/082; A61B 18/10; A61B 18/14; A61B 18/04; A61B 18/18; A61B 2018/1226; A61B 2018/00734; A61B 2018/00595; A61B 2018/4873; A61B 2017/0023; A61B 2017/00734; A61B 2019/307; A61B 2019/4873; A61B 17/320016
USPC .......................... 606/1, 27–52, 130, 169, 180
See application file for complete search history.

(56) References Cited

U.S. PATENT DOCUMENTS 2,994,324 A    8/1961   Lemos
3,234,356 A    2/1966   Babb
(Continued)

FOREIGN PATENT DOCUMENTS

CN    2715707 Y    8/2005
EP    1813200 A2   8/2007
(Continued)

OTHER PUBLICATIONS

European Search Report for European Application No. 12161530.6; dated Sep. 5, 2012; eight (8) pages.
(Continued)

*Primary Examiner* — Joseph Stoklosa
*Assistant Examiner* — Jocelyn D Ram
(74) *Attorney, Agent, or Firm* — Gerald E. Hespos; Michael J. Porco; Matthew T. Hespos

(57) ABSTRACT

A disposable cautery device and related methods for making and disassembling a disposable cautery device are disclosed. In one embodiment, the disposable cautery device comprises a housing having a first end and a second end. A cautery tip extends from the housing first end, and the housing second end is configured to receive a removable power source. An actuator is provided to selectively complete an electrical connection between the cautery tip and the removable power source. The actuator is disposed within a recess formed in the housing, and the recess is at least partially circumscribed by a raised rim. A top surface of the actuator is flush with or lower than the rim to inhibit inadvertent actuation of the disposable cautery device. In some embodiments, an end cap is coupled with the second end of the housing to retain the removable power source in the housing, and removal of the end cap from the housing causes the coupling between the end cap and the housing to fracture.

26 Claims, 14 Drawing Sheets

(51) Int. Cl.
*A61B 18/12* (2006.01)
*A61B 19/00* (2006.01)

(56) References Cited

U.S. PATENT DOCUMENTS

| | | | |
|---|---|---|---|
| 3,461,874 A | 8/1966 | Martinez | |
| 3,613,682 A | 10/1971 | Naylor | |
| D229,869 S | 1/1974 | Staub | |
| D232,591 S | 8/1974 | Haberman | |
| D240,277 S | 6/1976 | Staub | |
| 4,108,181 A * | 8/1978 | Saliaris | 606/30 |
| D253,303 S | 10/1979 | Barton et al. | |
| D254,150 S * | 2/1980 | Barton et al. | D24/144 |
| 4,359,052 A | 11/1982 | Staub | |
| 4,563,570 A | 1/1986 | Johns | |
| 4,606,342 A | 8/1986 | Zamba et al. | |
| 4,878,493 A | 11/1989 | Pasternak et al. | |
| 5,163,937 A | 11/1992 | Zamba | |
| 5,318,533 A | 6/1994 | Adams et al. | |
| 5,401,273 A | 3/1995 | Shippert | |
| 5,688,265 A * | 11/1997 | Citronowicz | 606/30 |
| D433,752 S | 11/2000 | Saravia | |
| 6,214,003 B1 | 4/2001 | Morgan et al. | |
| D449,395 S | 10/2001 | Dalton et al. | |
| 6,482,200 B2 | 11/2002 | Shippert | |
| 7,241,294 B2 * | 7/2007 | Reschke | 606/41 |
| 7,566,331 B2 * | 7/2009 | Looper et al. | 606/1 |
| 7,699,856 B2 | 4/2010 | Van Wyk et al. | |
| 7,699,859 B2 | 4/2010 | Bombard et al. | |
| 7,879,032 B1 | 2/2011 | Garito et al. | |
| 8,915,909 B2 | 12/2014 | Manwaring et al. | |
| 8,932,279 B2 | 1/2015 | Stringham et al. | |
| 2001/0027968 A1 | 10/2001 | Stuart | |
| 2003/0234632 A1 | 12/2003 | Fang | |
| 2004/0092992 A1 | 5/2004 | Adams et al. | |
| 2004/0126627 A1 | 7/2004 | Heine et al. | |
| 2005/0015080 A1 * | 1/2005 | Ciccone et al. | 606/30 |
| 2005/0159752 A1 | 7/2005 | Walker et al. | |
| 2005/0203546 A1 | 9/2005 | Van Wyk et al. | |
| 2006/0089622 A1 * | 4/2006 | Bourne et al. | 606/1 |
| 2008/0284372 A1 * | 11/2008 | Cover et al. | 320/112 |
| 2009/0112200 A1 * | 4/2009 | Eggers | 606/29 |
| 2009/0138006 A1 * | 5/2009 | Bales et al. | 606/33 |
| 2009/0171354 A1 | 7/2009 | Deville et al. | |
| 2009/0173804 A1 | 7/2009 | Kah, Jr. et al. | |
| 2009/0218207 A1 | 9/2009 | Mou | |
| 2009/0240246 A1 * | 9/2009 | Deville et al. | 606/33 |
| 2010/0004669 A1 | 1/2010 | Smith et al. | |
| 2010/0069940 A1 * | 3/2010 | Miller et al. | 606/169 |
| 2011/0064978 A1 | 3/2011 | McGahan et al. | |

FOREIGN PATENT DOCUMENTS

| | | |
|---|---|---|
| WO | WO0112090 | 2/2001 |
| WO | 200454626 A2 | 1/2004 |

OTHER PUBLICATIONS

Machine translation of CN 2715707 Y.
Chinese Search Report for Chinese Application No. 201210194072.5; dated Aug. 31, 2015; nine (9) pages.
English Translation of Chinese Search Report for Chinese Application No. 201210194072.5; dated Aug. 31, 2015; twelve (12) pages.

* cited by examiner

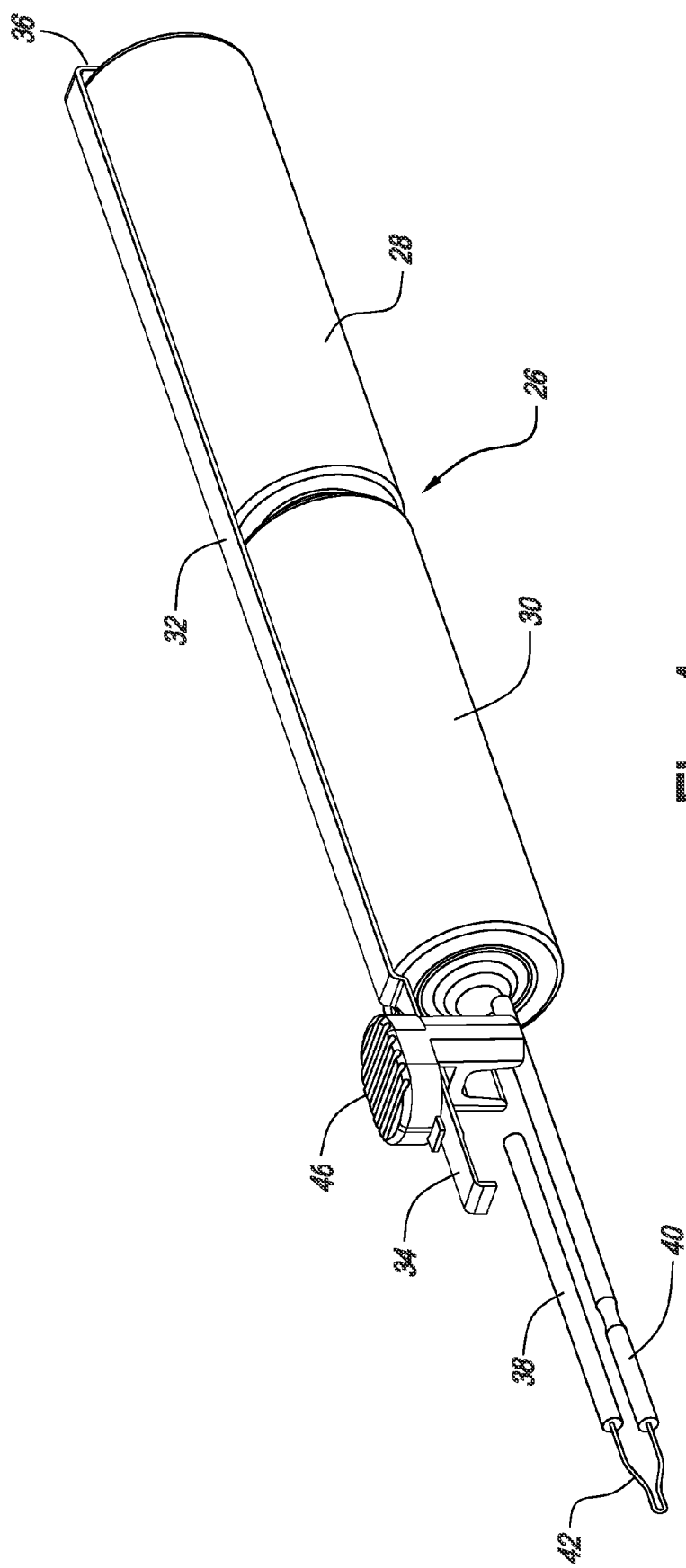

HAND-HELD CAUTERY DEVICE

FIELD OF THE INVENTION

The present invention relates to a battery-powered cautery device having certain improved features in comparison with the prior art.

BACKGROUND

A cautery is a medical instrument used to conduct heat to skin or flesh for medical reasons. For example, cauteries may be used to stop bleeding or to relieve fluid under a fingernail that is swollen from injury by burning a small hole through the nail. Cauteries are also commonly used to induce hemostasis in ophthalmic procedures and for parting sutures.

Often, cauteries are configured as hand-held devices including a cylindrical housing which surrounds one or more batteries. Typically, a metal-wire tip is in electrical communication with the batteries. A switch or button is used to selectively apply electrical current to and heat the metal-wire tip. During use, the heated tip can reach very high temperatures (e.g., 2200° F.).

To prevent contamination and because of the problems attendant to sterilization, cauteries are often disposable and may be designed for a single use. However, the actuation button or switch on prior art cautery devices can be easily (and unintentionally) depressed by a user or object. This creates a risk of accidental actuation of the cautery after disposal.

Moreover, prior art battery-operated cautery devices are typically constructed having a solid, single-piece housing surrounding the batteries. This makes removal of the batteries a complex and burdensome process.

SUMMARY

The present invention recognizes and addresses disadvantages of prior art constructions and methods. According to one embodiment, the present invention provides a disposable cautery device comprising a housing having a first end and a second end. The housing comprises an electrical circuit including an actuator and a removable power source. A cautery tip extends from the first end of the housing, and the cautery tip is in electrical communication with the electrical circuit. The actuator is configured to selectively complete the electrical circuit to actuate the cautery device. An end cap is attached to the second end of the housing via a fracturable coupling. The end cap is configured to retain the power source in the housing. The fracturable coupling breaks in a predetermined fashion in response to a predetermined force applied to the end cap.

According to a further embodiment, the present invention provides a disposable cautery device comprising a housing having a first end and a second end. A cautery tip extends from the housing first end, and the housing second end is configured to receive a removable power source. An actuator is provided to selectively complete an electrical connection between the cautery tip and the removable power source. The actuator is disposed within a recess formed in the housing, and the recess is at least partially circumscribed by a raised rim. A top surface of the actuator is flush with or lower than the rim to inhibit inadvertent actuation of the disposable cautery device. In some embodiments, an end cap is coupled with the second end of the housing to retain the removable power source in the housing, and removal of the end cap from the housing causes the coupling between the end cap and the housing to fracture.

According to a further embodiment, the present invention provides a method of disassembling a disposable cautery device. The method comprises providing a cautery device having a housing enclosing a removable power source. A first end of the housing comprises a cautery tip, a second end of the housing comprises at least one retaining member, and the at least one retaining member couples an end cap with the second end of the housing. The method also comprises applying a predetermined force to the end cap to cause the at least one retaining member to fracture, removing the end cap from the housing, and removing the removable power source from the housing. Thereby, the disposable cautery device is rendered inoperable and may be safely disposed of.

According to a further embodiment, the present invention provides a method of making a disposable cautery device. The method comprises providing a housing having a first end and a second end and providing an end cap configured to couple with the second end of the housing. The method also comprises providing at least one retaining member on one of the end cap and the housing second end. The at least one retaining member is fracturable in response to a predetermined force. Further, the method comprises defining at least one aperture in the other of the end cap and the housing second end. The at least one aperture is configured to engage the at least one retaining member. Finally, the method comprises coupling a cautery tip with the first end of the housing, inserting a removable power source into the housing such that the removable power source is in electrical communication with the cautery tip, and coupling the end cap to the second end of the housing such that the at least one retaining member engages the at least one aperture.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one of ordinary skill in the art, is set forth in the specification, which makes reference to the appended drawings, in which:

FIG. 4 is a perspective view of exemplary components of the electrical circuit of the disposable cautery device of FIG. 1.

Figure 1:
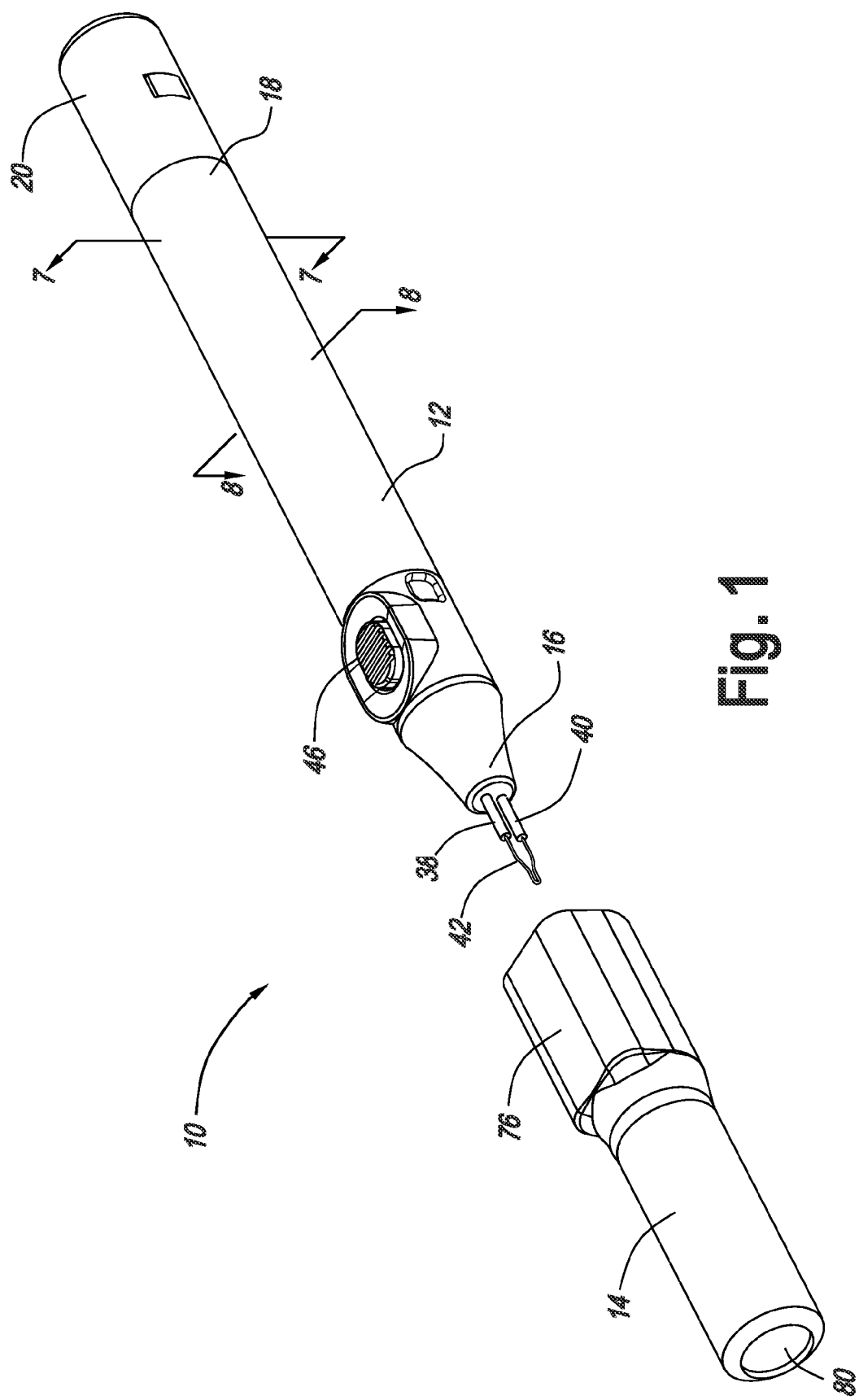
FIG. 1 is a perspective view of a disposable cautery device according to an embodiment of the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Embodiments of the present invention provide a disposable cautery device which comprises one or more features to inhibit inadvertent actuation of the cautery device. In one embodiment, the cautery device may include an actuator disposed in a recess defined by a raised portion of the cautery housing. In this regard, the housing may define a rim around the recess which inhibits accidental actuation of the cautery. As used herein, the term "actuator" refers to any suitable mechanism for actuating the cautery, including a button, switch, slider, trigger, or the like, which may be disposed in a recess in the cautery housing.

In another embodiment, the cautery device may include an end cap coupled with the housing of the cautery to retain a removable power source in the cautery housing. The end cap may be received on the housing via a fracturable coupling that is designed to fail when the end cap is removed from the housing. Because the end cap thus cannot be replaced after its removal, the removable power source is not retained in the housing and the cautery device cannot be reused. As used herein, a coupling is "fracturable" when it incorporates a designed failure mode in which the coupling breaks or fails in response to the application of a predetermined force. To facilitate description, the term "fracturable" may be interchangeable with the terms "breakable" and "frangible."

Some embodiments of the present invention are particularly suitable for use in a cautery device, and the below discussion will describe preferred embodiments in that context. However, those of skill in the art will understand that the present invention is not so limited. In fact, it is contemplated that the present invention be used with any appropriate handheld device including a removable power source for which appropriate disposal of the device is desirable. Thus, the present invention may be especially useful with "single-use" or non-reusable instruments.

Referring now to FIG. 1, according to one embodiment of the present invention, a disposable cautery device 10 may comprise a main unit having housing 12 to which a cover 14 may be attached. As shown, cautery device 10 may be a single temperature cautery, but embodiments of the present invention are also applicable to variable temperature cauteries. Housing 12, which may preferably be generally cylindrical and formed of a suitable nonconductive plastic material, may have a first end 16 and a second end 18. An end cap 20 may be located at second end 18 of housing 12.

Figure 2:
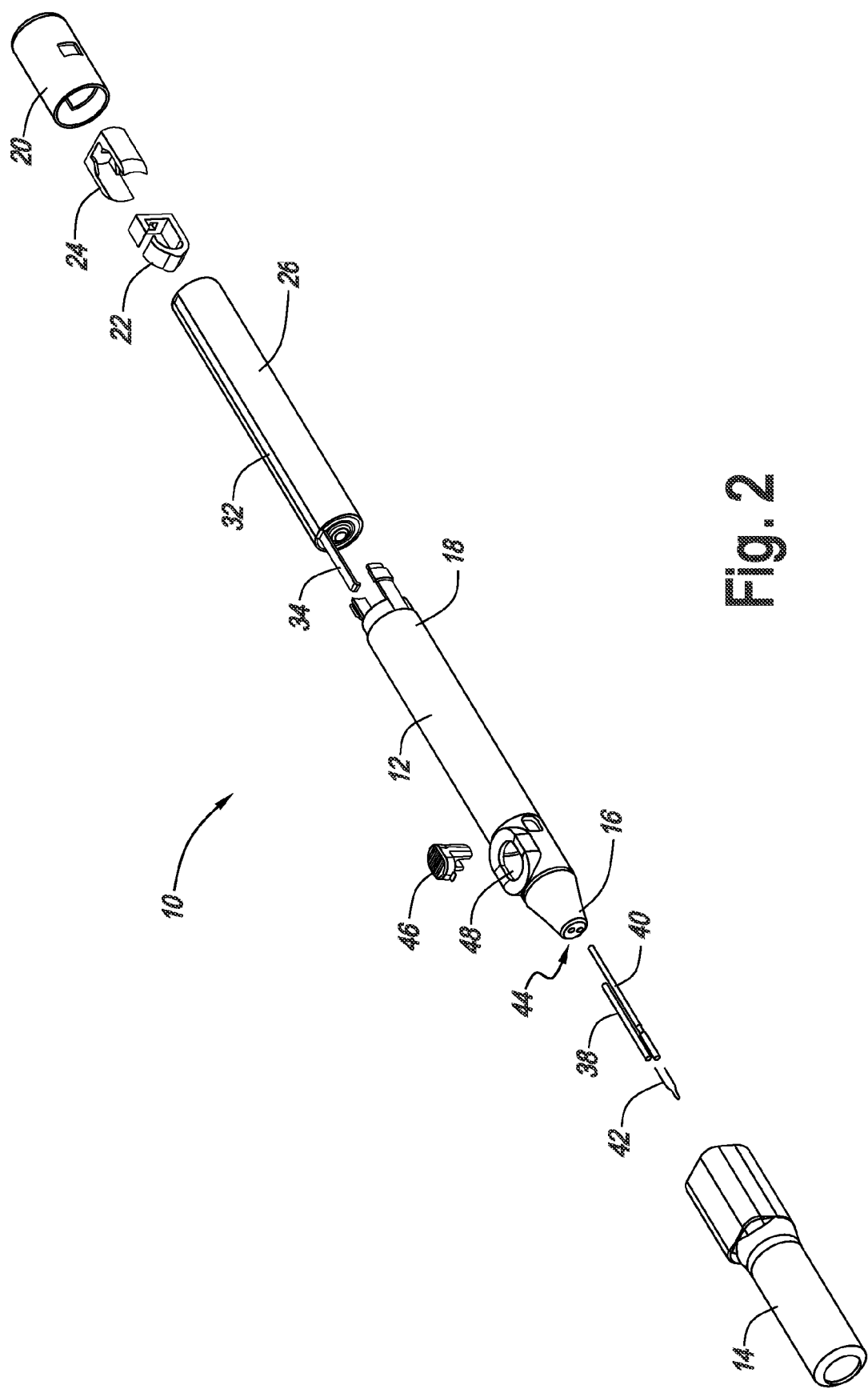
FIG. 2 is an exploded view of the disposable cautery device of FIG. 1.

Referring also to FIG. 2, which is an exploded view of the disposable cautery device of FIG. 1, end cap 20 receives a biasing member 22 and a support member 24. Biasing member 22 engages a power source 26 to retain it in place in housing 12 when end cap 20 is coupled with second end 18 of housing 12. Power source 26 may preferably comprise one or more removable batteries (such as AA or AAA batteries), but other power sources may be used. As shown in FIG. 4, power source 26 comprises two such batteries 28, 30 in this embodiment. Referring again also to FIG. 2, a conductor 32 extends along the length of power source 26. Conductor 32, which may comprise a substantially flat, elongate copper strip, defines a stepped front portion 34, and a rear portion 36 (FIG. 4) in contact with the negative terminal of one of the batteries of power source 26. A suitable heat-shrink material may be applied over the batteries and the portion of conductor 32 extending along the top of the batteries to affix conductor 32 to the batteries and maintain the batteries together as a unit.

Cautery device 10 may further comprise first and second electrodes 38, 40 which are operatively connected by a cautery tip 42. Electrodes 38, 40 may preferably be formed of brass, but other suitable conductive materials may be used. The length of second electrode 40 may be selected so that second electrode 40 is in electrical communication with the positive terminal of battery 30 when power source 26 is received in housing 12. As shown in FIG. 4, first electrode 38 is preferably shorter than second electrode 40 such that first electrode 38 is positioned below stepped front portion 34 of conductor 32 but does not contact the positive terminal of battery 30 when power source 26 is received in housing 12. Electrodes 38, 40 may be press fit into housing 12 via holes 44 defined in a front surface of first end 16. Those of skill in the art are familiar with other methods of coupling electrodes 38, 40 with housing 12, including insert molding.

Figure 3A:
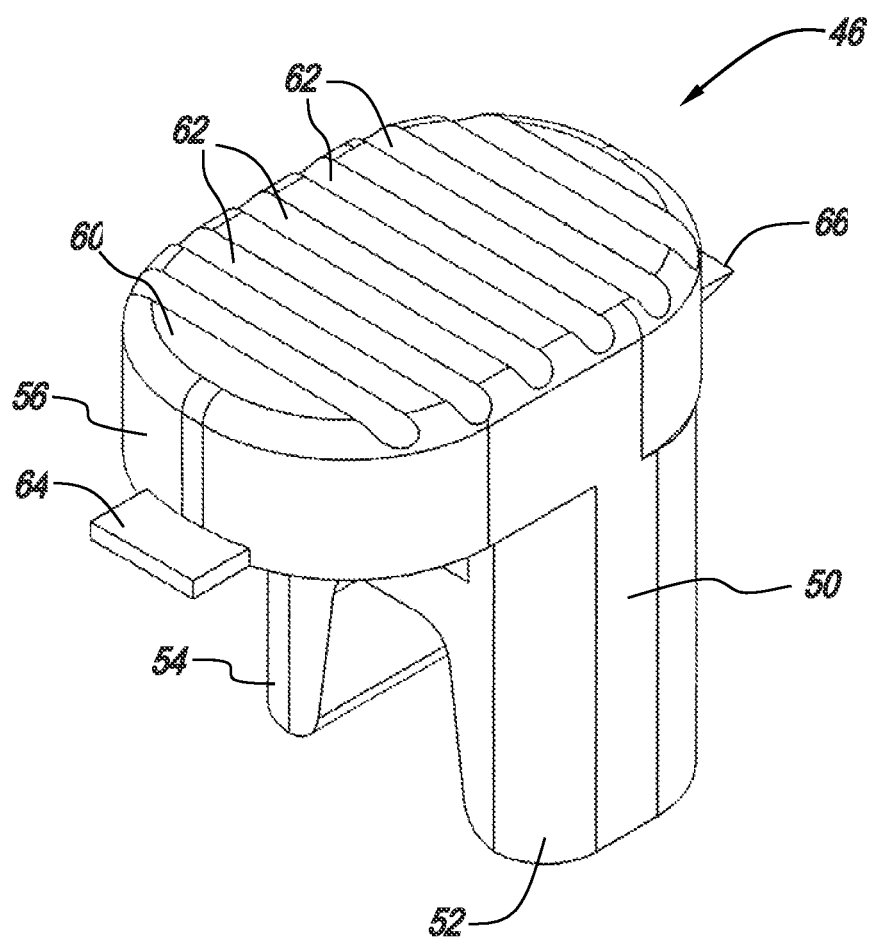
FIGS. 3A and 3B are respective isometric and front views of an actuator that may be used with the cautery device of FIG. 1.
Figure 3B:
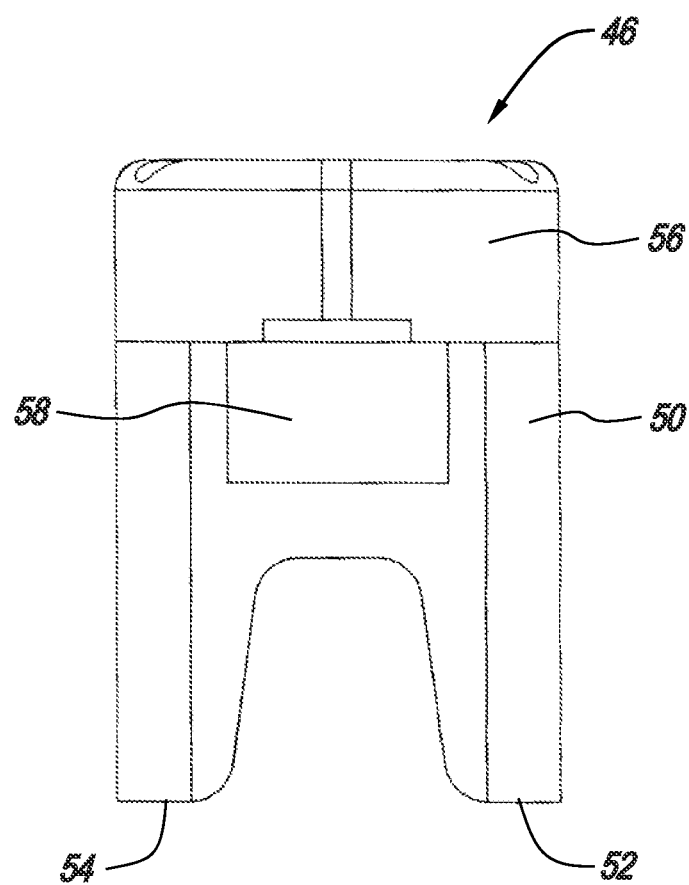

In addition, cautery device 10 may comprise an actuator 46 in register with an aperture 48 defined in housing 12. As described below, actuator 46 may preferably be disposed in a recess formed in a raised portion of housing 12. Referring now to FIGS. 3A and 3B, actuator 46, which may also be formed of a suitable nonconductive plastic material, may have an "H"-shaped frame 50 comprising legs 52, 54. A top portion 56 is disposed above frame 50 and defines an aperture 58 through actuator 46. As described in more detail below, stepped front portion 34 of conductor 32 is received through aperture 58 in this embodiment. A top surface 60 of actuator 46 may define a series of horizontal grooves 62 to provide a textured surface for a user's finger. Opposing tabs 64, 66 may extend from opposite ends of top portion 56. When actuator 46 is assembled with housing 12, tabs 64, 66 are located interior to housing 12 beyond the periphery of aperture 48 to limit the upward travel of actuator 46. Legs 52, 54 straddle second electrode 40 such that frame 50 may engage second electrode 40 to limit the downward travel of actuator 46. Because of its shorter length, first electrode 38 does not directly interfere with the vertical travel of actuator 46.

The operation of the electrical circuit of cautery device 10 is described with reference to FIG. 4. To facilitate illustration, the heat-shrink material over batteries 28, 30 and conductor 32 is not shown in FIG. 4. As noted above, the negative terminal of battery 28 of power source 26 is in electrical communication with conductor 32 via rear portion 36. Also, second electrode 40 is in electrical communication with the positive terminal of battery 30. Thus, when a user desires to actuate cautery 10, the user may apply a downward force on actuator 46, for example using his or her finger. This downward force causes stepped front portion 34 of conductor 32 to flex and come into contact with first electrode 38, thereby completing the electrical circuit. When the force is removed from actuator 46, stepped front portion 34 functions as a spring to return actuator 46 to its original position (i.e., with tabs 64, 66 abutting the interior surface of housing 12). Thus, actuator 46 may be used to selectively complete the electrical circuit and heat cautery tip 42.

Figure 5:
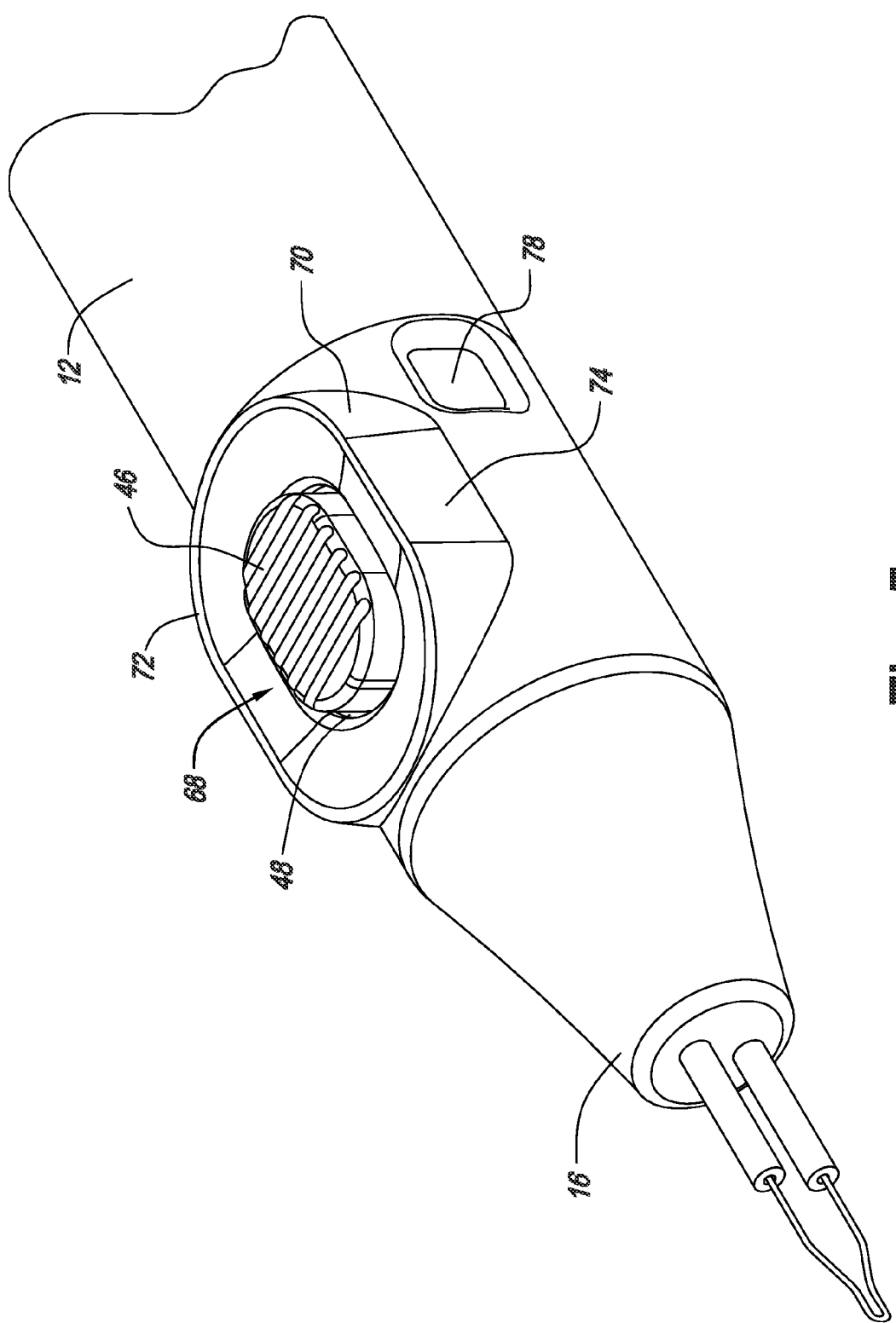
FIG. 5 is an enlarged perspective view of an actuator disposed within a recess formed in the housing of the disposable cautery device of FIG. 1.

Referring now to FIG. 5, actuator 46 is disposed in this embodiment within a recess 68 formed in housing 12. In particular, housing 12 may preferably define a protrusion (or raised portion) 70 forming recess 68. Although protrusion 70 may take any suitable shape, as shown it may resemble a rounded rectangle or oval. In this regard, protrusion 70 defines a rim 72 which surrounds recess 68. In one embodiment, the sides 74 of protrusion 70 may be substantially parallel with planes perpendicular to the plane of rim 72 and tangent to housing 12. However, those of skill in the art will appreciate that protrusion 70 may be larger or smaller as needed or desired.

Referring again also to FIG. 1, cover 14, which is also generally cylindrical, may define a portion 76 configured to be received over protrusion 70. Thus, cautery device 10 cannot be actuated when cover 14 is in place on housing 12. Further, cover 14 may define on its interior surface one or more raised tabs which register with one or more slots 78 formed in housing 12. Thereby, cover 14 may be retained on housing 12 until sufficient force is applied to remove the tabs from slots 78. Cover 14 may also define an aperture 80 in its end surface to allow air circulation.

In a preferred embodiment, protrusion 70 may be sized such that the top surface 60 of actuator 46 (FIG. 3A) may be flush with or lower than rim 72. As a result, to actuate cautery device 10, a force must be applied over an area within the periphery of rim 72. If a force is applied over an area larger than or equal in dimension to rim 72, actuator 46 will not be depressed and cautery device 10 will not be actuated. For example, in the absence of protrusion 70 and rim 72 surrounding actuator 46, if a cautery device rolled over onto its side on a surface (e.g., a waste container, a table, or a user's skin), the actuator could be inadvertently depressed. In the illustrated embodiment, however, the surface would contact rim 72 without actuating cautery device 10. Accordingly, embodiments of the present invention may reduce the risk of inadvertent actuation of cautery device 10.

Figure 6:
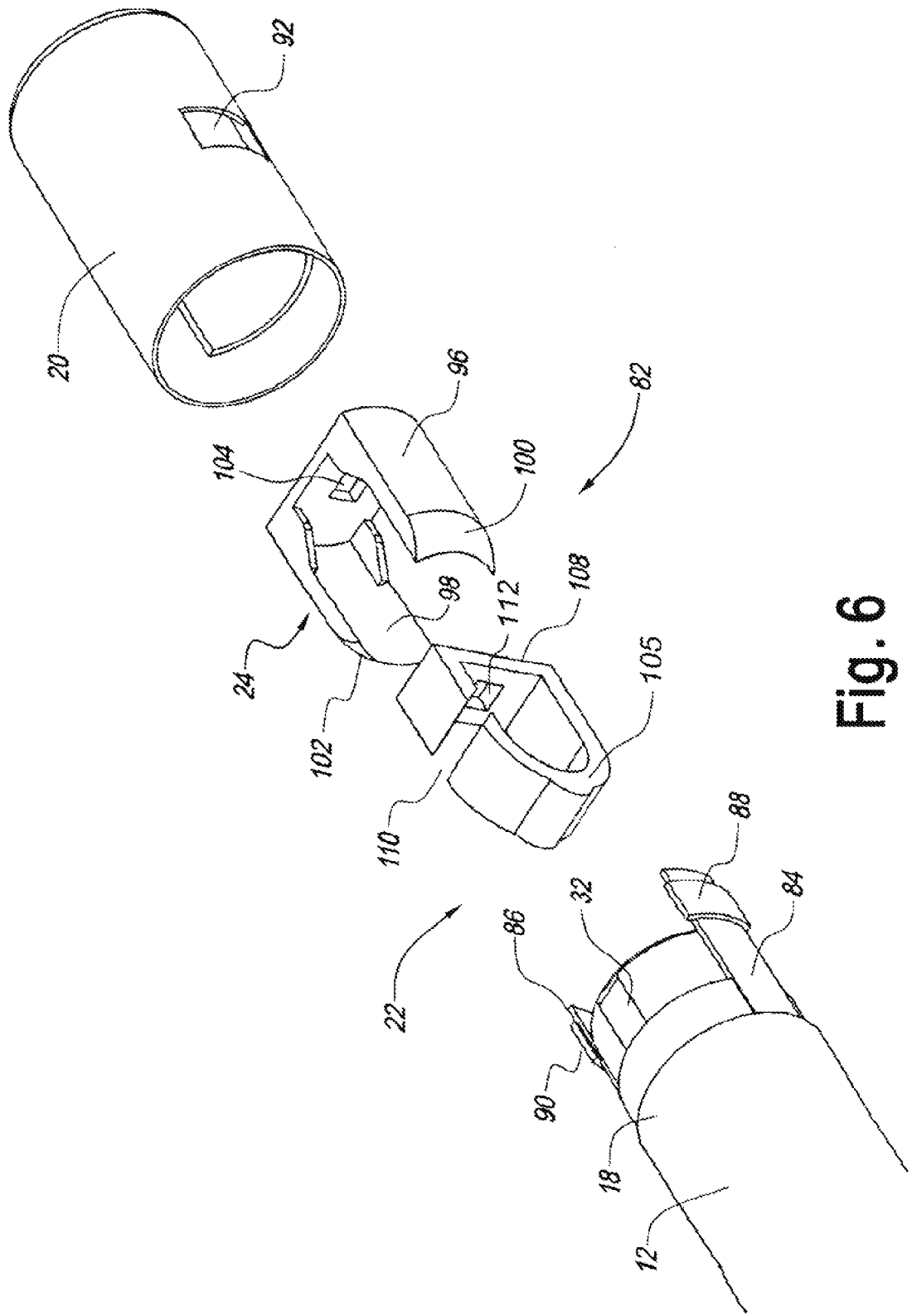
FIG. 6 is an enlarged exploded view of a fracturable coupling between the end cap and the housing of the disposable cautery device of FIG. 1.
Figure 7:
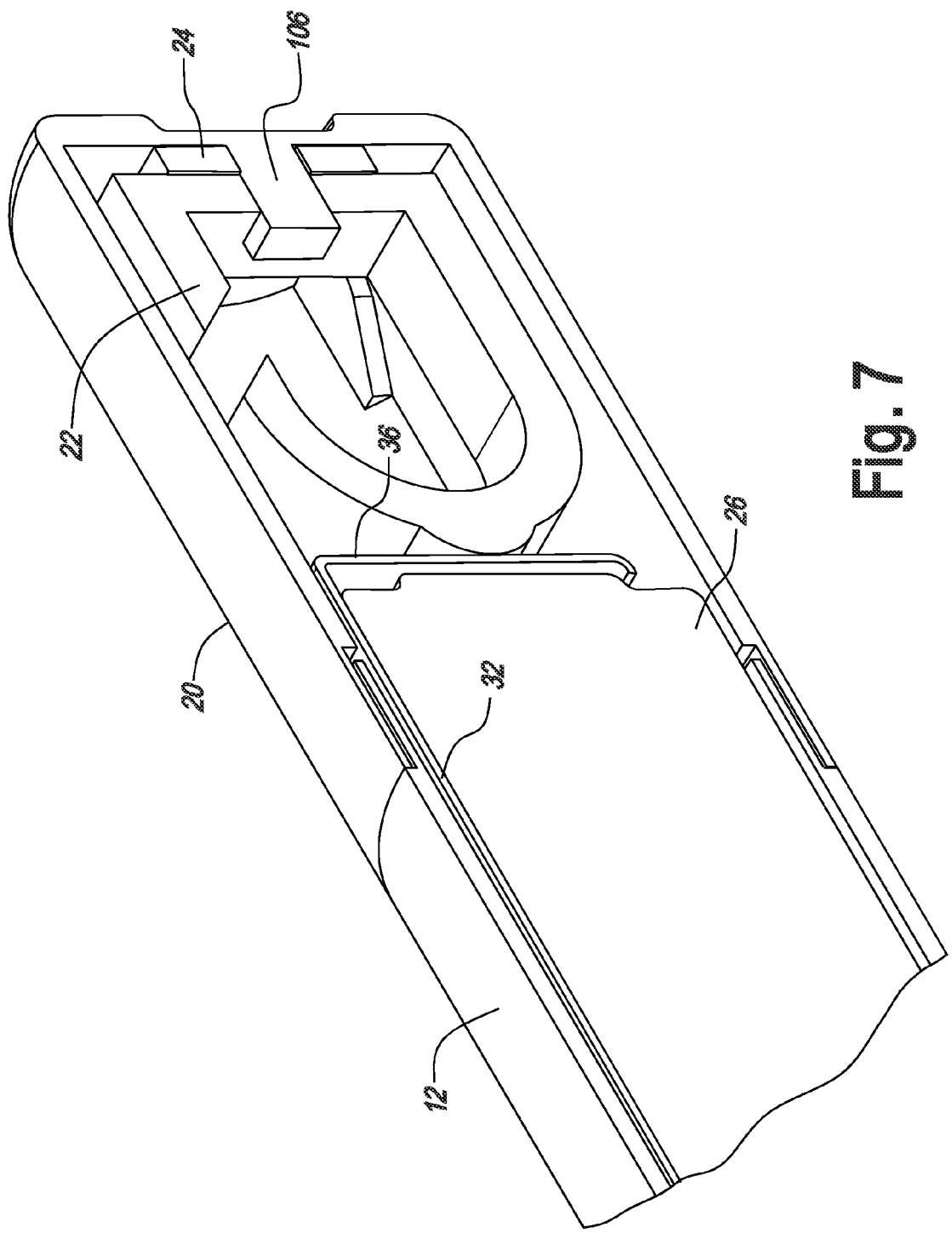
FIG. 7 is a cross-sectional view taken along the line 7-7 of FIG. 1.
Figure 8:
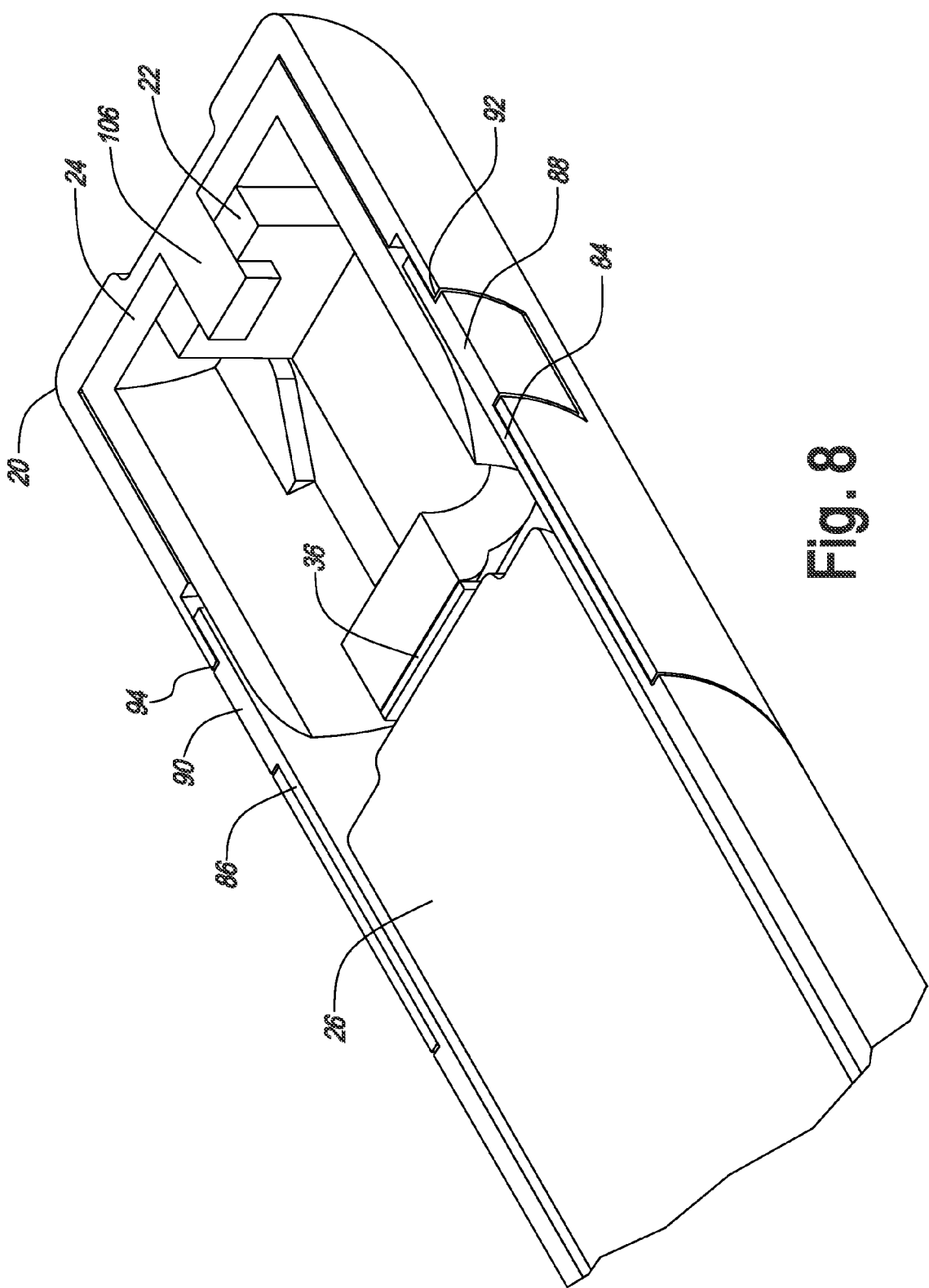
FIG. 8 is a cross-sectional view taken along the line 8-8 of FIG. 1.

One embodiment of a feature for destructive disassembly of cautery device 10 can be described with reference to FIGS. 6-8. FIG. 6 is an enlarged exploded view of a fracturable coupling, generally indicated at 82, between end cap 20 and housing 12 of cautery device 10. FIG. 7 is a cross-sectional view taken along the line 7-7 of FIG. 1. FIG. 8 is a cross-sectional view taken along the line 8-8 of FIG. 1.

More particularly, fracturable coupling 82 may comprise one or more retaining members extending from second end 18 of housing 12. Here, two laterally-opposed retaining members 84, 86 are provided and may be formed of the same material as housing 12. Retaining members 84, 86 may preferably respectively define raised tabs 88, 90 which register with apertures 92, 94 defined in end cap 20. Importantly, retaining members 84, 86 are preferably designed to fracture in response to the application of a predetermined force applied to end cap 20.

Retaining members 84, 86 may also be flexible and preferably biased slightly outward at an oblique angle to the longitudinal axis of housing 12. This may enable tabs 88, 90 to "snap" into place in apertures 92, 94 during assembly. The horizontal distance between the periphery of retaining members 84, 86 (when flexed to be substantially parallel with the longitudinal axis of housing 12) is preferably slightly less than the inner diameter of end cap 20. Thus, end cap 20 may be snugly received over retaining members 84, 86. Likewise, the horizontal distance between the periphery of tabs 88, 90 is preferably approximately equal to the outer diameter of end cap 20.

As will be appreciated, tabs 88, 90 and apertures 92, 94 may take any suitable shape. As shown, tabs 88, 90 and apertures 92, 94 may be substantially square, but these elements may also be circular or oval-shaped, for example. Moreover, in alternative embodiments, in place of apertures 92, 94, end cap 20 may define a slot, groove, or any structure which suitably engages retaining members 84, 86 as described in more detail below.

Fracturable coupling 82 may further comprise support member 24. Support member 24, which may be substantially "U"-shaped and formed of nonconductive plastic, preferably defines legs 96, 98 having respective camming surfaces 100, 102. Support member 24 may further define an aperture 104 sized for removable receipt on a peg 106 defined in end cap 20 (FIGS. 7-8). The horizontal distance between the periphery of legs 96, 98 is preferably slightly less than the horizontal distance between the inner surfaces of retaining members 84, 86. Thus, as shown in FIG. 8, when end cap 20 is coupled with housing 12, retaining members 84, 86 may be positioned between legs 96, 98 and end cap 20. Camming surfaces 100, 102 may slidably engage retaining members 84, 86 to facilitate coupling of end cap 20 and housing 12.

When support member 24 is received in end cap 20 via aperture 104 and peg 106 and end cap 20 is coupled with second end 18 of housing 12, support member 24 resists an inward force that may be applied to either or both of tabs 88, 90 that would otherwise disengage tabs 88, 90 from apertures 92, 94 and allow end cap 20 to be removed from housing 12. This discourages a user attempting to disassemble cautery device 10 from trying to remove end cap 20 without fracturing either or both of retaining members 84, 86.

In use, to disassemble cautery device 10, a user may apply a predetermined force to end cap 20 relative to housing 12. For example, the user may apply a torque to end cap 20, causing tabs 88, 90 to interfere with end cap 20. When the torque reaches a predetermined level, either or both of retaining members 84, 86 may fracture in response. This allows a user to remove end cap 20 from retaining members 84, 86 and second end 18 of housing 12. Then, the user may remove power source 26 from housing 12 to disable cautery device 10. Consequently, when cautery device 10 is disposed of, it cannot be inadvertently actuated. Further, because either or both of retaining members 84, 86 is fractured, a user cannot reassemble end cap 20 with housing 12 in an attempt to reuse cautery device 10.

In an alternative embodiment, fracturable coupling 82 may be reversed. For example, end cap 20 may define one or more retaining members and second end 18 of housing 12 may define one or more corresponding apertures or the like. Those of skill in the art will appreciate that coupling 82 in this embodiment may function substantially as described above.

In this embodiment, end cap 20 also receives a biasing member 22. Biasing member 22 may be springlike and define a semicircular front portion 105, and a substantially square rear portion 108. A gap 110 may be defined on one side of biasing member 22 between front portion 105 rear portion 108 to allow front portion 105 to bow or flex in response to a force applied to front portion 105. For example, when end cap 20 is coupled with housing 12, biasing member 22 may bow or flex as it biases power source 26 into electrical communication with second electrode 40.

Biasing member 22 is inserted in end cap 20 so that it is perpendicular to and nests within support member 24. In particular, biasing member 22 may define an aperture 112 in rear portion 108 sized for removable receipt on peg 106 between legs 96, 98 of support member 24. This arrangement is illustrated in further detail in FIG. 7. In a preferred embodiment, biasing member 22 may be formed of a nonconductive plastic material. Notably, this may be desirable to prevent corrosion from power source 26 that may occur with springs formed of a metallic material.

Figure 9:
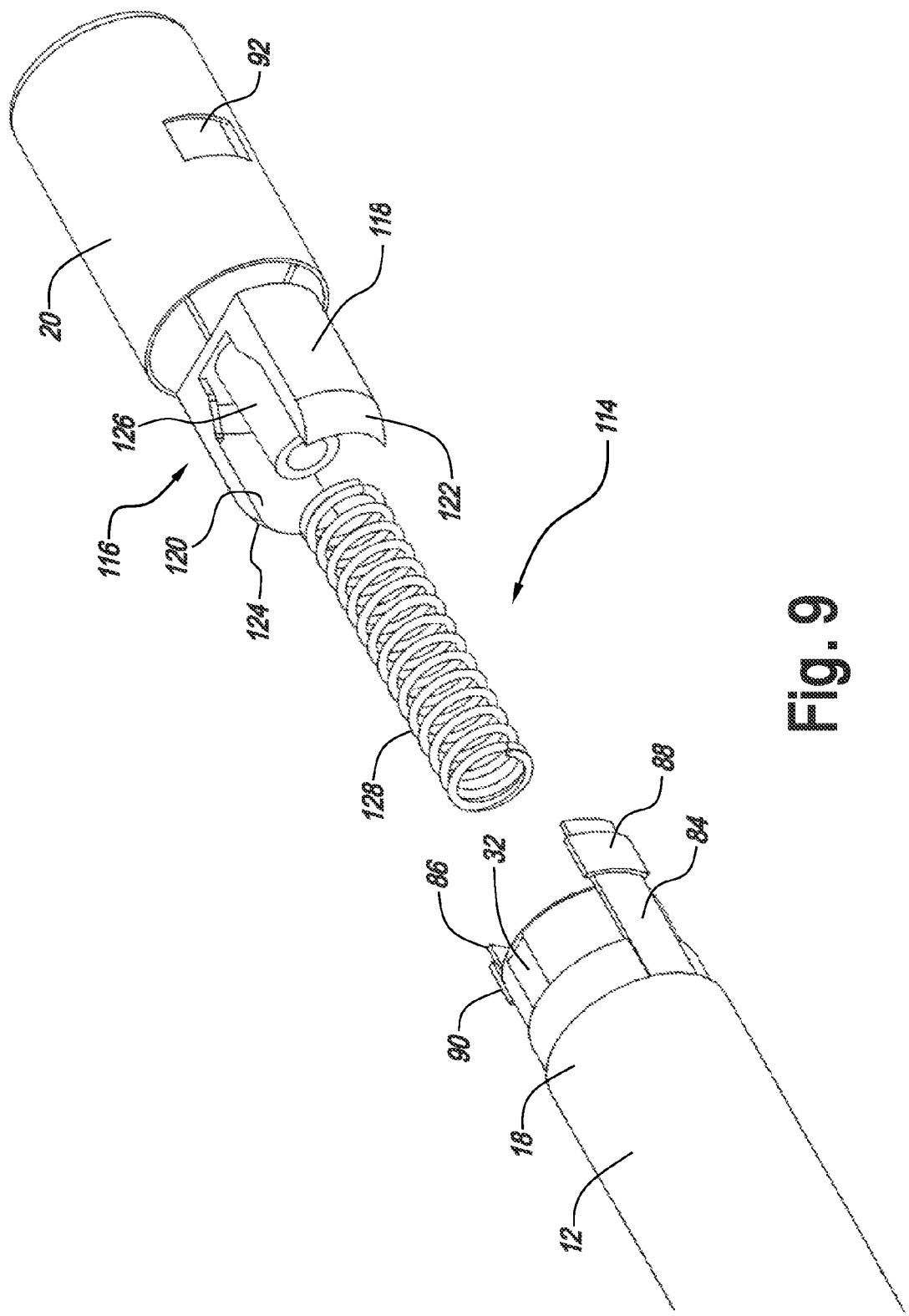
FIG. 9 is an enlarged exploded view of a fracturable coupling between the end cap and the housing of a disposable cautery device according to an alternative embodiment of the present invention.
Figure 10:
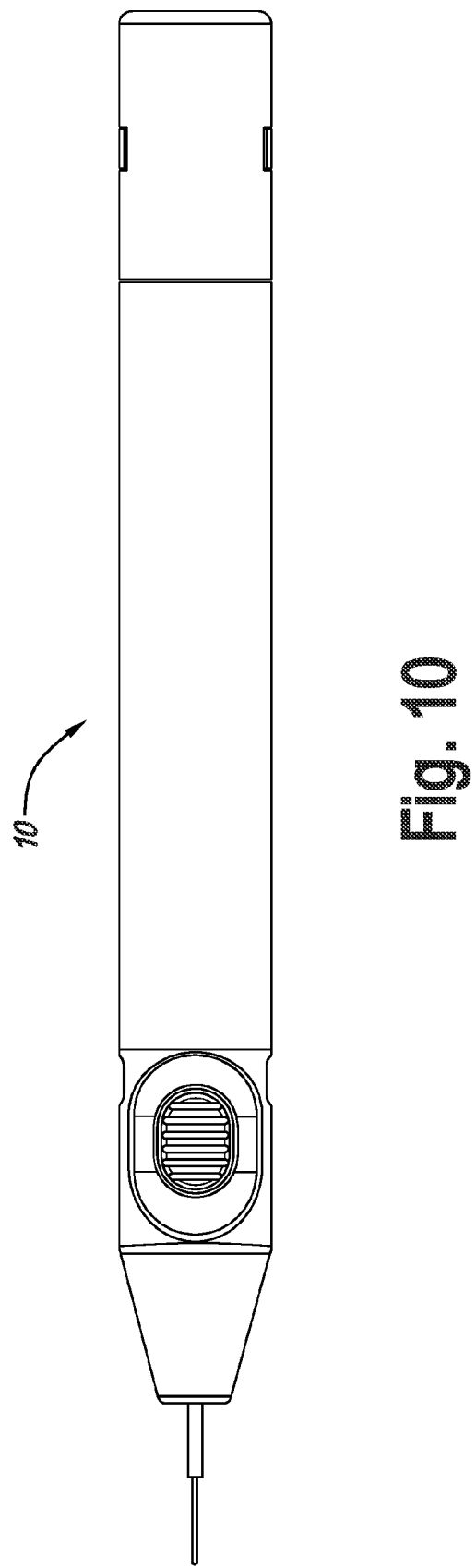
FIG. 10 is a top view of the disposable cautery device of FIG. 1.
Figure 11:
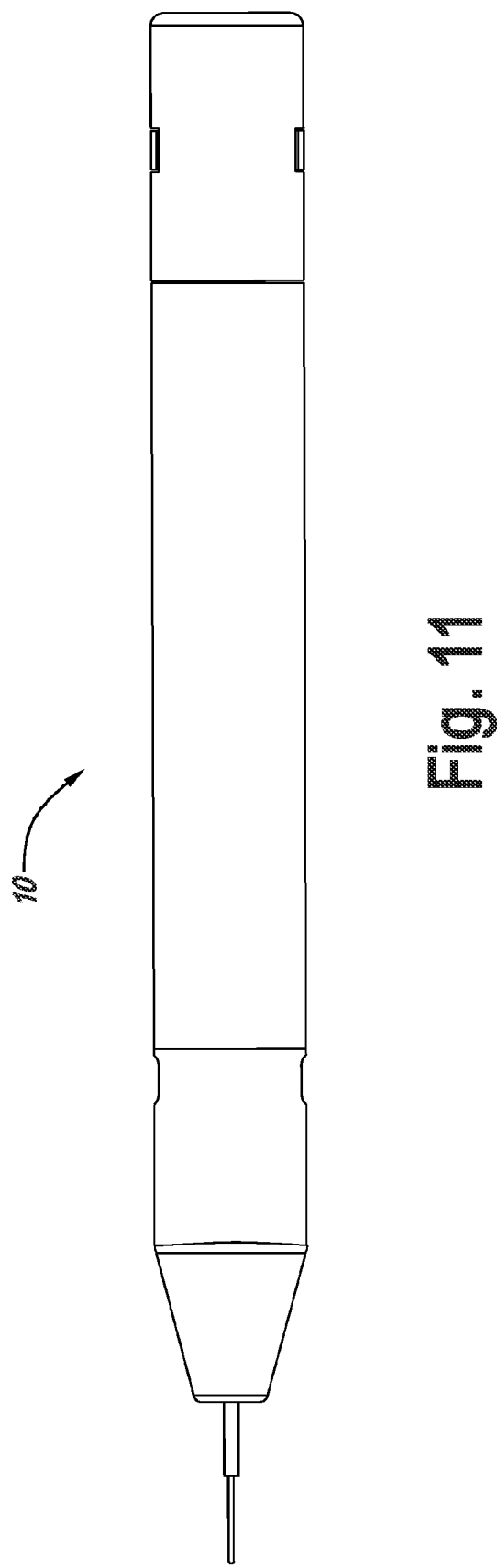
FIG. 11 is a bottom view of the disposable cautery device of FIG. 1.
Figure 12:
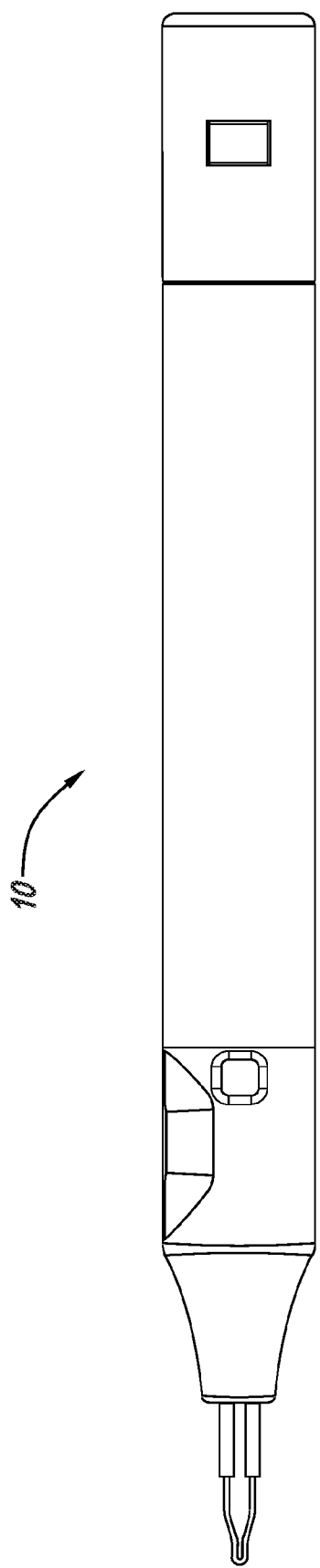
FIG. 12 is a right side view of the disposable cautery device of FIG. 1, with the left side being a mirror image thereof.
Figure 13:
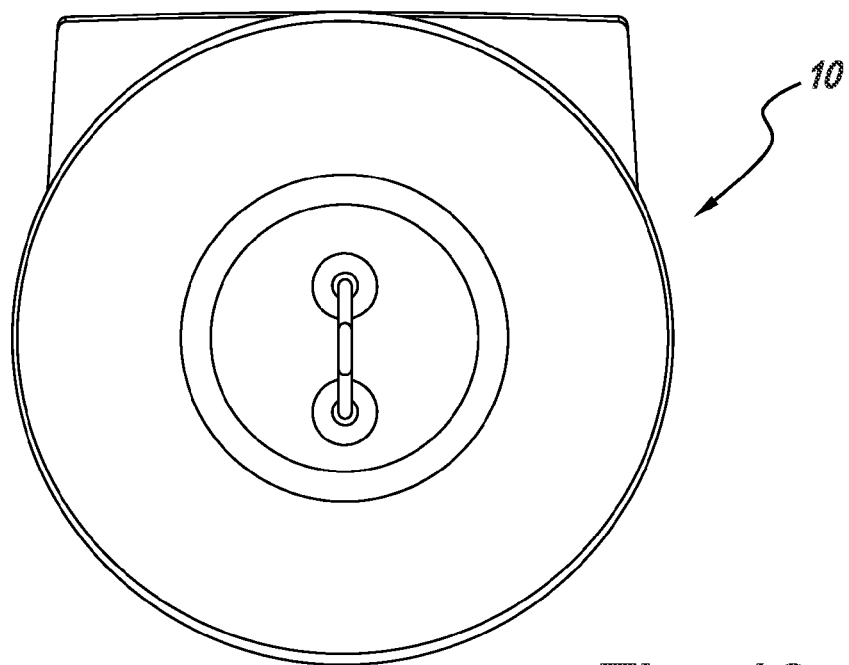
FIG. 13 is a front view of the disposable cautery device of FIG. 1.
Figure 14:
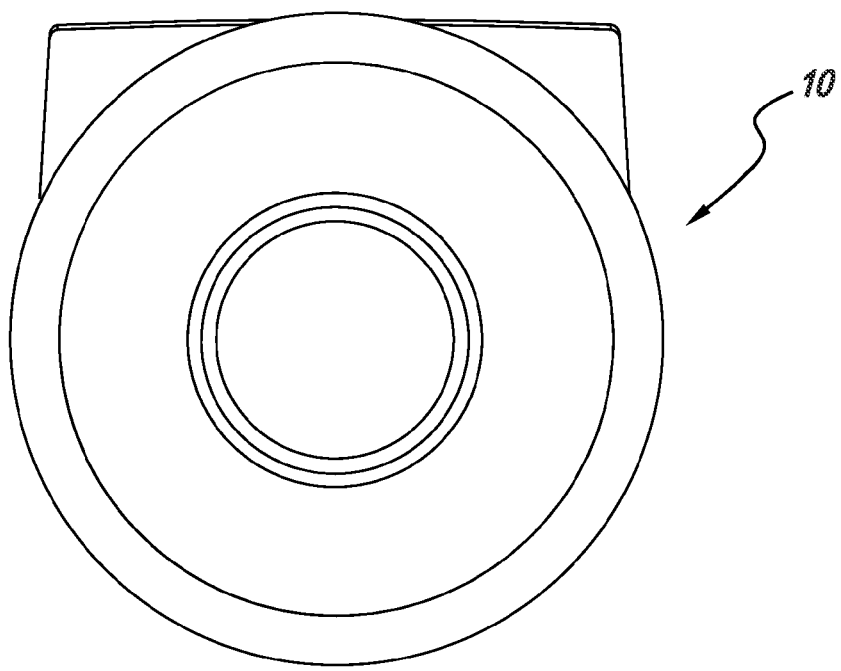
FIG. 14 is a back view of the disposable cautery device of FIG. 1.

An alternative embodiment of a fracturable coupling can be described with reference to FIG. 9. FIG. 9 is an enlarged exploded view of a fracturable coupling, generally indicated at 114, between end cap 20 and housing 12 of cautery device 10. Fracturable coupling 114 may be similar in many respects to fracturable coupling 82, and thus fracturable coupling 114 may comprise retaining members 84, 86 defining raised tabs 88, 90 which register with apertures 92, 94 defined in end cap 20, as described above. In this embodiment, however, fracturable coupling 114 may comprise a support member 116. As with support member 24, support member 116 may be substantially "U"-shaped and formed of nonconductive plastic. Further, support member 116 may define legs, 118, 120 having respective camming surfaces 122, 124 and may further define an aperture for removable receipt on peg 106 in end cap 20, as described above. Support member 116 may thus function in an analogous fashion to support member 24 to discourage a user from attempting to disassemble cautery device 10 without fracturing either or both of retaining members 84, 86.

In this embodiment, however, support member 116 preferably defines a frustoconical projection 126 on which a spring 128 may be carried. As shown, projection 126 may be hollow to receive peg 106 therein. Spring 128 may be press-fit onto projection 126 and, when end cap 20 is coupled with housing 12, engage a back surface of power source 26 to bias power source 26 into electrical communication with second electrode 40. Additionally, unlike biasing member 22, spring 128 may be formed of a metallic material, which may be desirable in some embodiments of cautery device 10.

While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. A disposable cautery device, comprising:
   a housing having a first end and a second end, said housing comprising an electrical circuit including an actuator and a removable power source;
   a cautery tip extending from said first end of said housing, said cautery tip in electrical communication with said electrical circuit; and
   an end cap configured to be received by and attached to said second end of said housing via a fracturable coupling, said end cap configured to retain said power source in said housing during use of the disposable cautery device, said fracturable coupling comprises retaining members and apertures, wherein said retaining members extend from said second end of said housing, wherein said apertures are formed in said end cap and are configured to receive said retaining members;
   wherein said actuator is configured to selectively complete said electrical circuit to actuate said cautery device;
   wherein said fracturable coupling breaks in a predetermined fashion in response to a predetermined force applied to said end cap;
   wherein said fracturable coupling attaches said end cap to said second end of said housing in such a way that disconnection of said end cap from said second end of said housing to remove said removable power source involves breaking said fracturable coupling.

2. The disposable cautery device of claim 1, wherein said actuator is retained in a recess formed in said housing.

3. The disposable cautery device of claim 2, wherein said housing defines a rim surrounding said recess.

4. The disposable cautery device of claim 3, wherein a top surface of said actuator is flush with or lower than said rim.

5. The disposable cautery device of claim 1, wherein said fracturable coupling comprises at least two retaining members extending from said second end.

6. The disposable cautery device of claim 1, wherein said fracturable coupling comprises at least one retaining member defining a raised tab which registers with an aperture defined in said end cap.

7. The disposable cautery device of claim 6, wherein said tab interferes with said disconnection of said end cap to cause said at least one retaining member to fracture when said predetermined force is applied to said end cap.

8. The disposable cautery device of claim 1, wherein said actuator is a button.

9. The disposable cautery device of claim 1, wherein said housing is cylindrical.

10. The disposable cautery device of claim 1, further comprising a cover configured to be received on said first end of said housing to enclose said cautery tip and said actuator.

11. The disposable cautery device of claim 1, wherein said removable power source is reusable after being removed from said housing, while said disposable cautery device is rendered inoperable.

12. A disposable cautery device, comprising:
   a housing having an interior, a first end, and a second end;
   a cautery tip extending from the first end of the housing, the second end of the housing being configured to receive a removable power source entirely within the interior of the housing;
   an actuator configured to selectively complete an electrical connection between the cautery tip and the removable power source, wherein the actuator is retained in a recess formed in the housing; and
   an end cap configured to be received by the second end of the housing and configured to be connected to the second end of the housing via a coupling during use of the disposable cautery device, the end cap configured to retain the removable power source entirely within the interior of the housing during use of the disposable cautery device;
   wherein the recess is at least partially circumscribed by a raised rim;

wherein, when no force is applied to the actuator, a top surface of the actuator is flush with or lower than the raised rim to inhibit inadvertent actuation of the disposable cautery device;

wherein the coupling comprises laterally-opposed retaining members extending from the second end of the housing in a proximal direction, each of the retaining members comprising a tab raised above a surface of the retaining member;

wherein the end cap comprises laterally-opposed apertures configured to receive the tabs of the retaining members to connect the end cap to the second end of the housing; and wherein the coupling is configured to connect the end cap to the second end of the housing in such a way that disconnection of the end cap from the second end of the housing to remove the removable power source from the interior of the housing involves breaking the coupling.

13. The disposable cautery device of claim 12, wherein at least one of the retaining members is fracturable in response to a predetermined force applied to the end cap.

14. The disposable cautery device of claim 13, wherein the tab of each retaining member interferes with the disconnection of the end cap to cause at least one of the retaining members to fracture when the predetermined force is applied to the end cap.

15. The disposable cautery device of claim 12, wherein the removable power source is reusable after being removed from the housing, while the disposable cautery device is rendered inoperable.

16. A disposable cautery device comprising:
a housing having an interior, a first end, and a second end;
a cautery tip extending from the first end of the housing;
a removable power source configured to provide power to the cautery tip;
an end cap configured to be connected to the second end of the housing to retain the removable power source in the interior of the housing;
a biasing member configured to retain the removable power source entirely within the interior of the housing when the end cap is connected to the second end of the housing; and
a fracturable coupling configured to enable the end cap to be connected to the second end of the housing;
wherein removal of the removable power source involves breaking the fracturable coupling.

17. The disposable cautery device of claim 16, further comprising an actuator configured to complete an electrical circuit with the cautery tip and removable power source.

18. The disposable cautery device of claim 17, wherein the actuator is disposed in a recess formed in a top surface of the housing, the recess being at least partially circumscribed by a raised rim such that a top surface of the actuator is flush with or lower than the raised rim to inhibit inadvertent actuation of the disposable cautery device.

19. The disposable cautery device of claim 16, wherein breaking the fracturable coupling disconnects the end cap from the second end of the housing.

20. The disposable cautery device of claim 16, wherein the fracturable coupling comprises at least one retaining member and at least one aperture, the at least one retaining member defined by one of the end cap and the housing, and the at least one aperture defined by the other of the end cap and the housing.

21. The disposable cautery device of claim 20, wherein the at least one retaining member is fracturable in response to a predetermined force applied to the end cap.

22. The disposable cautery device of claim 21, wherein the predetermined force is a torque force.

23. The disposable cautery device of claim 16, wherein the removable power source is reusable after being removed from the housing, while the disposable cautery device is rendered inoperable.

24. A disposable cautery device comprising:
a housing having an interior, a first end, and a second end;
a cautery tip extending from the first end of the housing;
a removable power source configured to provide power to the cautery top;
an end cap configured to be connected to the second end of the housing to retain the removable power source in the interior of the housing; and
a fracturable coupling configured to enable the end cap to be connected to the second end of the housing, the fracturable coupling comprises retaining members and apertures, wherein the retaining members extend from the second end of the housing, wherein the apertures are formed in the end cap and are configured to receive the retaining members,
wherein removal of the removable power source involves breaking the fracturable coupling.

25. The disposable cautery device of claim 24, wherein each retaining member comprises a raised tab configured for insertion in the apertures.

26. The disposable cautery device of claim 25, further comprising a support member retained in the end cap, wherein the support member is configured to prevent the raised tabs from being removed from the apertures without fracturing at least one of the retaining members.

* * * * *